(12) United States Patent
Goldstein et al.

(10) Patent No.: US 8,716,215 B2
(45) Date of Patent: May 6, 2014

(54) METHOD OF TREATING OR PREVENTING TISSUE DETERIORATION, INJURY OR DAMAGE DUE TO A NEURO-, MUSCULAR- OR NEURO-MUSCULAR-DEGENERATIVE DISEASE, OR RESTORE TISSUE ADVERSELY AFFECTED BY SAID DISEASE

(75) Inventors: Allan L. Goldstein, Washington, DC (US); Jack Finkelstein, Jr., Chevy Chase, MD (US)

(73) Assignee: Regenerx Biopharmaceuticals, Inc., Rockville, MD (US)

( * ) Notice: Subject to any disclaimer, the term of this patent is extended or adjusted under 35 U.S.C. 154(b) by 1428 days.

(21) Appl. No.: 11/813,264

(22) PCT Filed: Jan. 13, 2006

(86) PCT No.: PCT/US2006/001255
§ 371 (c)(1),
(2), (4) Date: Apr. 2, 2008

(87) PCT Pub. No.: WO2006/076588
PCT Pub. Date: Jul. 20, 2006

(65) Prior Publication Data
US 2008/0274098 A1   Nov. 6, 2008

Related U.S. Application Data
(60) Provisional application No. 60/643,307, filed on Jan. 13, 2005.

(51) Int. Cl.
*A61K 38/00* (2006.01)
*A61K 39/395* (2006.01)
*A61P 3/04* (2006.01)
*A61P 25/00* (2006.01)
*C07K 14/47* (2006.01)

(52) U.S. Cl.
USPC ........ 514/1.1; 424/130.1; 514/17.7; 514/17.9

(58) Field of Classification Search
CPC .............. A61K 38/08; A61K 38/2292; G01N 33/5058; G01N 33/5061
See application file for complete search history.

(56) References Cited

U.S. PATENT DOCUMENTS

2003/0060405 A1   3/2003   Kleinman et al.
2004/0220111 A1   11/2004  Kleinman et al.

FOREIGN PATENT DOCUMENTS

| JP | 04-234325 A | 8/1992 | |
| JP | 4234325 | * 8/1992 | ............ A61K 37/02 |
| WO | 0006190 A1 | 2/2000 | |
| WO | 2004/099768 A1 | 11/2004 | |

OTHER PUBLICATIONS

Pryce et al. Cannabinoids inhibit neurodegeneration in models of multiple sclerosis. Brain. 2003. vol. 126, pp. 2191-2202.*
Ethgen et al. Degenerative musculoskeletal disease. Ann Rheum Dis 2004. vol. 63, pp. 1-3.*
Grounds. REasons for degeneration of ageing skeletal muscle: a central role for IGF-1 signalling. Bioegrontology. 2002. vol. 3, pp. 19-24.*
Gilleard. Is Alzheimer's disease preventable? A review of two decades of epidemiological research. Aging and Mental Health. 2000. vol. 4, No. 2, pp. 101-118.*
Abstract in English for JP-4234325, 2 Pages.*
Matsumoto et al. Japanese Kakai Patent Publication No. H04-234325, 1992. English translation. 8 pages.*
Matsumoto et al. Translated by Schreiber Translations. JP PN 04234325, 1992, English translation, 17 pages.*
Akiyama et al. Inflammation and Alzheimer's disease. Neurobiology of Aging, 2000, vol. 21, pp. 383-421.*
McGeer et al. Inflammation and neurodegeneration in Parkinson's disease. Parkinsonism and Related Disorders. 2004, vol. 10, pp. S3-S7.*
McGeer et al. Inflammatory Processes in Amyothrophic Lateral Sclerosis. Oct. 2002. Muscle and Nerve. vol. 26, pp. 459-470.*
Supplementary European Search Report issued in EP Appln. No. 06718342.6, dated Apr. 3, 2012, 7 pages.
Rizvi et al., "Current approved options for treating patients with multiple sclerosis", Neurology, 2004, Dec. 2004, 63 (12 Suppl 6): S8-14, Abstract only.
Mexican Office Action for patent application No. MX/a/2007/008464 dated Apr. 5, 2013 with English translation (9 pgs).

* cited by examiner

*Primary Examiner* — Marcela M Cordero Garcia
(74) *Attorney, Agent, or Firm* — Rothwell, Figg, Ernst & Manbeck, P.C.

(57) ABSTRACT

A method of treatment for treating, preventing, inhibiting or reducing tissue deterioration, injury or damage due to a neuro-, muscular- or neuro-muscular-degenerative disease, or for restoring tissue adversely affected by said disease, in a subject, includes administering to a subject in need of such treatment an effective amount of a composition including a peptide agent including amino acid sequence LKKTET or LKKTNT, a conservative variant thereof, or a peptide agent that stimulates production of an LKKTET or LKKTNT peptide, or a conservative variant thereof, in the tissue.

38 Claims, No Drawings

METHOD OF TREATING OR PREVENTING TISSUE DETERIORATION, INJURY OR DAMAGE DUE TO A NEURO-, MUSCULAR- OR NEURO-MUSCULAR-DEGENERATIVE DISEASE, OR RESTORE TISSUE ADVERSELY AFFECTED BY SAID DISEASE

CROSS-REFERENCE TO RELATED APPLICATIONS

The present application is a National Phase of International Application Serial No. PCT/US2006/001255, filed 13 Jan. 2006, and claims benefit of U.S. Provisional Application 60/643,307, filed Jan. 13, 2005.

BACKGROUND OF THE INVENTION

1. Field of the Invention

The present invention relates to the field of treating or preventing tissue deterioration, injury or damage due to a neuro-, muscular- or neuro-muscular-degenerative disease, or restoring tissue adversely affected by said disease.

2. Description of the Background Art

Neuro-degenerative diseases, muscular-degenerative diseases and neuro-muscular-degenerative diseases are debilitating diseases that can destroy memory, brain functions, muscle functions and other physiological functions of a subject. Such diseases may be genetic, or result from exposure by a subject to factors in the environment, contaminated food, and the like. Such diseases may include Alzheimer's disease, multiple sclerosis (MS), Lou Gehrig's disease (amytrophic lateral sclerosis or ALS), Parkinson's disease, spinal muscular atrophy (SMA), myasthenia gravis, autism, muscular dystrophy, transmissible spongiform encephalopathies (TSEs) including bovine spongiform encephalopathy (BSE), and the like.

Muscular dystrophies are genetic disorders characterized by progressive muscle wasting and weakness that begin with microscopic changes in the muscle. As muscles degenerate over time, the person's muscle strength declines.

Duchenne muscular dystrophy (DMD) is one of a group of muscular dystrophies characterized by the enlargement of muscles. DMD is one of the most prevalent types of muscular dystrophy and is characterized by rapid progression of muscle degeneration that occurs early in life. All are X-linked and affect mainly males—an estimated 1 in 3500 boys worldwide.

The gene for DMD, found on the X chromosome, encodes a large protein—dystrophin. Dystrophin is required inside muscle cells for structural support; it is thought to strengthen muscle cells by anchoring elements of the internal cytoskeleton to the surface membrane. Without it, the cell membrane becomes permeable, so that extracellular components enter the cell, increasing the internal pressure until the muscle cell "explodes" and dies. The subsequent immune response can add to the damage.

Becker muscular dystrophy (BMD) is a much milder version of DMD. Its onset is usually in the teens or early adulthood, and the course is slower and far less predictable than that of DMD.

In the U.S., there are over 84,000 patients with degenerative muscular dystrophy diseases.

There remains a need in the art for methods of treatment for treating, preventing, inhibiting or reducing tissue deterioration, injury or damage due to a neuro-, muscular- or neuro-muscular-degenerative disease, or for restoring tissue adversely affected by said disease.

SUMMARY OF THE INVENTION

In accordance with one aspect, a method of treatment for treating, preventing, inhibiting or reducing tissue deterioration, injury or damage due to a neuro-, muscular- or neuro-muscular-degenerative disease, or for restoring tissue adversely affected by said disease, in a subject, comprises administering to a subject in need of such treatment an effective amount of a composition comprising a peptide agent comprising amino acid sequence LKKTET (SEQ ID NO:1) or LKKTNT (SEQ ID NO:2), a conservative variant thereof, or a stimulating agent that stimulates production of an LKKTET (SEQ ID NO:1) or LKKTNT (SEQ ID NO:2) peptide, or a conservative variant thereof, in said tissue, so as to inhibit said tissue deterioration, injury or damage due to a neuro-, muscular- or neuro-muscular-degenerative disease, or restore tissue adversely affected by said disease.

DETAILED DESCRIPTION OF THE INVENTION

Without being found to any specific theory, actin-sequestering peptides such as thymosin beta 4 (Tβ4 or TB4) and other agents including actin-sequestering peptides or peptide fragments containing amino acid sequence LKKTET (SEQ ID NO:1) or LKKTNT (SEQ ID NO:2) or conservative variants thereof, promote reversal or prevention of tissue deterioration, injury or damage due to a neuro-, muscular- or neuro-muscular-degenerative disease.

Thymosin beta 4 was initially identified as a protein that is up-regulated during endothelial cell migration and differentiation in vitro. Thymosin beta 4 was originally isolated from the thymus and is a 43 amino acid, 4.9 kDa ubiquitous polypeptide identified in a variety of tissues. Several roles have been ascribed to this protein including a role in a endothelial cell differentiation and migration, T cell differentiation, actin sequestration, vascularization and wound healing.

Neuro-, muscular- or neuro-muscular-degenerative diseases to which the invention is applicable include, but are not limited to, Alzheimer's disease, multiple sclerosis, Lou Gehrig's disease, Parkinson's disease, spinal muscular atrophy, myasthenia gravis, autism, muscular dystrophy (including DMD and BMD), transmissible spongiform encephalopathies (TSEs) including BSE, the like. Such diseases may be associated with inflammatory disorders. Accordingly, the invention is particularly applicable to inflammation-associated neuro-, muscular-, or neuro-muscular-degenerative diseases. According to one embodiment, the invention is applicable to neuro-, muscular- or neuro-muscular-degenerative diseases other than muscular dystrophy.

In accordance with one embodiment, the invention is a method of treatment for treating, preventing, inhibiting or reducing tissue deterioration, injury or damage due to a neuro-, muscular- or neuro-muscular-degenerative disease, or for restoring tissue adversely affected by said disease, in a subject, comprising administering to a subject in need of such treatment an effective amount of a composition comprising a peptide agent, which may be a polypeptide comprising amino acid sequence LKKTET (SEQ ID NO: 1) or LKKTNT (SEQ ID NO: 2), or a conservative variant thereof having neuro-, muscular-, and/or neuro-muscular-degenerative disease-inhibiting activity, preferably Thymosin β4, and/or Tβ4 isoforms, analogues or derivatives, including KLKKTET (SEQ ID NO: 3), LKKTETQ (SEQ ID NO: 4), N-terminal variants of T134, C-terminal variants of Tβ4 and antagonists of Tβ4.

The invention also may utilize oxidized Tβ4. In accordance with other embodiments, the agent is other than thymosin beta 4 or than oxidized Tβ4.

Compositions which may be used in accordance with the present invention include peptide agents such as Thymosin β4 (Tβ4), and/or Tβ4 isoforms, analogues or derivatives, including oxidized Tβ4, N-terminal variants of Tβ4, C-terminal variants of Tβ4 and antagonists of Tβ4, polypeptides or peptide fragments comprising or consisting essentially of the amino acid sequence LKKTET (SEQ ID NO:1) or conservative variants thereof, having neuro-, muscular-, and/or neuro-muscular-degenerative disease-inhibiting activity. International Application Serial No. PCT/US99/17282, incorporated herein by reference, discloses isoforms of Tβ4 which may be useful in accordance with the present invention as well as amino acid sequence LKKTET (SEQ ID NO: 1) and conservative variants thereof, which may be utilized with the present invention. International Application Serial No. PCT/GB99/00833 (WO 99/49883), incorporated herein by reference, discloses oxidized Thymosin β4 which may be utilized in accordance with the present invention. Although the present invention is described primarily hereinafter with respect to Tβ4 and Tβ4 isoforms, it is to be understood that the following description is intended to be equally applicable to amino acid sequence LKKTET (SEQ ID NO: 1) or LKKTNT (SEQ ID NO: 2), peptides and fragments comprising or consisting essentially of LKKTET (SEQ ID NO: 1) or LKKTNT (SEQ ID NO: 2), conservative variants thereof having neuro-, muscular-, and/or neuro-muscular-degenerative disease-inhibiting activity, and/or Tβ4 isoforms, analogues or derivatives, including N-terminal variants of Tβ4, C-terminal variants of Tβ4 and antagonists of Tβ4. The invention also may utilize oxidized Tβ4.

In one embodiment, the invention provides a method of treatment for treating, preventing, inhibiting or reducing tissue deterioration, injury or damage due to a neuro-, muscular- or neuro-muscular-degenerative disease other than muscular dystrophy, or for restoring tissue adversely affected by said disease, in a subject, comprising administering to a subject in need of such treatment an effective amount of a composition comprising a peptide agent comprising amino acid sequence LKKTET (SEQ ID NO: 1) or LKKTNT (SEQ ID NO: 2), a conservative variant thereof, or a stimulating agent that stimulates production of an LKKTET (SEQ ID NO: 1) or LKKTNT (SEQ ID NO: 2) peptide, or a conservative variant thereof, in said tissue, so as to inhibit said tissue deterioration, injury or damage due to a neuro-, muscular- or neuro-muscular-degenerative disease, or restore tissue adversely affected by said disease. In another embodiment, the disease is other than Duchene muscular dystrophy.

In another embodiment, the invention provides a method of treatment for treating, preventing, inhibiting or reducing tissue deterioration, injury or damage due to a disease comprising muscular dystrophy, or for restoring tissue adversely affected by said disease, in a subject, comprising administering to a subject in need of such treatment an effective amount of a composition comprising a peptide agent other than TB4 comprising amino acid sequence LKKTET (SEQ ID NO: 1) or LKKTNT SEQ ID NO: 2), a conservative variant thereof, or a stimulating agent that stimulates production of an LKKTET (SEQ ID NO: 1) or LKKTNT (SEQ ID NO: 2) peptide, or a conservative variant thereof, in said tissue, so as to inhibit said tissue deterioration, injury or damage due to a neuro-, muscular- or neuro-muscular-degenerative disease, or restore tissue adversely affected by said disease.

In one embodiment, the invention provides a method of treatment for treating, preventing, inhibiting or reducing tissue deterioration, injury or damage due to a neuro-, muscular- or neuro-muscular-degenerative disease, or for restoring tissue adversely affected by said disease, in a subject, by contacting the tissue with an effective amount of a composition which contains a peptide agent as described herein. As non-limiting examples, the tissue may be selected from neural and/or muscular tissue of said subject. The contacting may be directly or systemically. Examples of direct administration include, for example, contacting the tissue, by direct application or inhalation, with a solution, lotion, salve, gel, cream, paste, spray, suspension, dispersion, hydrogel, ointment, or oil comprising a peptide agent as described herein. Systemic administration includes, for example, intravenous, intraperitoneal, intramuscular injections of a composition containing a peptide agent as described herein, in a pharmaceutically acceptable carrier such as water for injection.

Peptide agents for use in the invention, as described herein, may be administered in any effective amount. For example, a peptide agent as described herein may be administered in dosages within the range of about 0.0001-1,000,000 micrograms, more preferably in amounts within the range of about 0.1-5,000 micrograms, most preferably within the range of about 1-30 micrograms.

A composition in accordance with the present invention can be administered daily, every other day, every other week, every other month, etc., with a single application or multiple applications per day of administration, such as applications 2, 3, 4 or more times per day of administration.

Many Tβ4 isoforms have been identified and have about 70%, or about 75%, or about 80% or more homology to the known amino acid sequence of Tβ4. Such isoforms include, for example, Tβ4$^{ala}$, Tβ9, Tβ10, Tβ11, Tβ12, Tβ13, Tβ14 and Tβ15. Similar to Tβ4, the Tβ10 and Tβ15 isoforms have been shown to sequester actin. Tβ4, Tβ10 and Tβ15, as well as these other isoforms share an amino acid sequence, LKKTET (SEQ ID NO: 1) or LKKTNT (SEQ ID NO: 2), that appears to be involved in mediating actin sequestration or binding. Although not wishing to be bound by any particular theory, the activity of peptide agents as described herein may be due, at least in part, to the anti-inflammatory activity of such agents. Tβ4 also can modulate actin polymerization (e.g. β-thymosins appear to depolymerize F-actin by sequestering free G-actin). Tβ4's ability to modulate actin polymerization may be due to its ability to bind to or sequester actin via the LKKTET (SEQ ID NO: 1) or LKKTNT (SEQ ID NO: 2) sequence. Thus, as with Tβ4, other proteins which are anti-inflammatory and/or bind or sequester actin, or modulate actin polymerization, including Tβ4 isoforms having the amino acid sequence LKKTET (SEQ ID NO: 1) or LKKTNT (SEQ ID NO: 2), are likely to be effective, alone or in a combination with Tβ4, as set forth herein.

Peptide agents as described herein, can prevent and/or limit the apoptic death of brain and other neurovascular cells and tissue by upregulating metabolic and signaling enzymes such as the phosphatidylinositol 3-kinase (P13-K)/Akt (protein kinase β) pathway. Upregulating P13-K)/Akt and downstream phosphorylated Bad and proline rich Akt survival kinase protects neuronal cells. In addition peptide agents as described herein, such as Tβ4 and Tβ4 isoforms or oxidized forms of Tβ4 by virtue of their ability to down-regulate inflammatory cytokines such as IL-18 and chemokines such as IL-8 and enzymes such as caspace 2, 3, 8 and 9 protects neuronal cells and facilitates healing of nervous tissue.

Peptide agents as described herein, can decrease inflammatory chemokine, cytokine and capase activity.

Peptide agents as described herein, can prevent neurotoxicity in the brain and spinal cord by preventing glutamate induced neurotoxicity. Uncontrolled release of glutamate, an excitatory neurotransmitter, from damaged brain and nervous tissues is a primary mediator of mitochondrial dysfunction and energy mechanisms in the cell which results in several inflammatory reactions, mechanical stress altered trophic signals and death of affected nervous cells and tissues.

Thus, it is specifically contemplated that known LKKTET (SEQ ID NO: 1) or LKKTNT (SEQ ID NO: 2) peptides as described herein, including Tβ4 isoforms, such as Tβ4$^{ala}$, Tβ9, Tβ10, Tβ11, Tβ12, Tβ13, Tβ14 and Tβ15, as well as Tβ4 isoforms not yet identified, will be useful in the methods of the invention. As such LKKTET (SEQ ID NO: 1) or LKKTNT (SEQ ID NO: 2) peptides as describes herein, including Tβ4 isoforms are useful in the methods of the invention, including the methods practiced in a subject. The invention therefore further provides pharmaceutical compositions comprising LKKTET (SEQ ID NO: 1) or LKKTNT (SEQ ID NO: 2) peptides as described herein, including Tβ4, as well as Tβ4 isoforms Tβ4$^{ala}$, Tβ9, Tβ10, Tβ11, Tβ12, Tβ13, Tβ14 and Tβ15, and a pharmaceutically acceptable carrier.

In addition, other agents or proteins having anti inflammatory activity and/or actin sequestering or binding capability, or that can mobilize actin or modulate actin polymerization, as demonstrated in an appropriate sequestering, binding, mobilization or polymerization assay, or identified by the presence of an amino acid sequence that mediates actin binding, such as LKKTET (SEQ ID NO: 1) or LKKTNT (SEQ ID NO: 2), for example, can similarly be employed in the methods of the invention. Such proteins may include gelsolin, vitamin D binding protein (DBP), profilin, cofilin, depactin, DnaseI, vilin, fragmin, severin, capping protein, β-actinin and acumentin, for example. As such methods include those practiced in a subject, the invention further provides pharmaceutical compositions comprising gelsolin, vitamin D binding protein (DBP), profilin, cofilin, depactin, DnaseI, vilin, fragmin, severin, capping protein, p-actinin and acumentin as set forth herein. Thus, the invention includes the use of an polypeptide comprising the amino acid sequence LKKTET (SEQ ID NO: 1) or LKKTNT (SEQ ID NO: 2) and conservative variants thereof.

As used herein, the term "conservative variant" or grammatical variations thereof denotes the replacement of an amino acid residue by another, biologically similar residue. Examples of conservative variations include the replacement of a hydrophobic residue such as isoleucine, valine, leucine or methionine for another, the replacement of a polar residue for another, such as the substitution of arginine for lysine, glutamic for aspartic acids, or glutamine for asparagine, and the like.

Tβ4 has been localized to a number of tissue and cell types and thus, agents which stimulate the production of an LKKTET (SEQ ID NO: 1) or LKKTNT (SEQ ID NO: 2) peptide such as Tβ4 or another peptide agent as described herein, can be added to or comprise a composition to effect production a peptide agent from a tissue and/or a cell. Such stimulating agents may include members of the family of growth factors, such as insulin-like growth factor (IGF-1), platelet derived growth factor (PDGF), epidermal growth factor (EGF), transforming growth factor beta (TGF-β), basic fibroblast growth factor (bFGF), thymosin α1 (Tα1) and vascular endothelial growth factor (VEGF). More preferably, the stimulating agent is transforming growth factor beta (TGF-β) or other members of the TGF-β superfamily.

In accordance with one embodiment, subjects are treated with a stimulating agent that stimulates production in the subject of a peptide agent as defined herein.

Additionally, other agents that assist in reduction of tissue deterioration, injury or damage due to a neuro-, muscular- or neuro-muscular-degenerative disease, or restoring tissue adversely affected by said disease may be added to a composition along with a peptide agent as described herein. For example, and not by way of limitation, a peptide agent as described herein alone or in combination can be added in combination with any one or more of the following agents: antibiotics, VEGF, KGF, FGF, PDGF, TGFβ, IGF-1, IGF-2, IL-1, prothymosin α and/or thymosin α1 in an effective amount.

The invention also includes a pharmaceutical composition comprising a therapeutically effective amount of a peptide agent as described herein in a pharmaceutically acceptable carrier.

The actual dosage or reagent, formulation or composition that provides treatment may depend on many factors, including the size and health of a subject. However, persons of ordinary skill in the art can use teachings describing the methods and techniques for determining clinical dosages as disclosed in PCT/US99/17282, supra, and the references cited therein, to determine the appropriate dosage to use.

Suitable formulations may include a peptide agent as described herein at a concentration within the range of about 0.001-50% by weight, more preferably within the range of about 0.01-0.1% by weight, most preferably about 0.05% by weight.

The therapeutic approaches described herein involve various routes of administration or delivery of a peptide agent as described herein, including any conventional administration techniques (for example, but not limited to, direct administration, local injection, inhalation, or systemic administration), to a subject. The methods and compositions using or containing a peptide agent as described herein may be formulated into pharmaceutical compositions by admixture with pharmaceutically acceptable non-toxic excipients or carriers.

The invention includes use of antibodies which interact with, enhance or inhibit a peptide agent as described herein. Antibodies which consist essentially of pooled monoclonal antibodies with different epitopic specificities, as well as distinct monoclonal antibody preparations are provided. Monoclonal antibodies are made from antigen containing fragments of the protein by methods well known to those skilled in the art as disclosed in PCT/US99/17282, supra. The term antibody as used in this invention is meant to include monoclonal and polyclonal antibodies.

In yet another embodiment, the invention provides a method of treating a subject by administering an effective amount of stimulating agent which modulates gene expression. The term "modulate" refers to inhibition or suppression of expression when a peptide agent as described herein is over expressed, and induction of expression when a peptide agent as described herein is underexpressed. The term "effective amount" means that amount of stimulating agent which is effective in modulating gene expression of a peptide agent as described herein, resulting in reducing the symptoms of tissue deterioration, injury or damage due to a neuro-, muscular- or neuro-muscular-degenerative disease, or restoring tissue adversely affected by said disease. A stimulating agent which modulates gene expression of a peptide agent as described herein may be a polynucleotide, for example. The polynucleotide may be an antisense, a triplex agent, or a ribozyme. For example, an antisense directed to the structural gene region or to the promoter region of a peptide agent as described herein may be utilized. The stimulating agent which modulates gene expression of a peptide agent as described herein may also be a small interfering RNAs (siRNAs).

In another embodiment, the invention provides a method for utilizing compounds that modulate activity of a peptide agent as described herein. Compounds that affect activity of a peptide agent as described herein (e.g., antagonists and agonists) include peptides, peptidomimetics, polypeptides, chemical compounds, minerals such as zincs, and biological agents.

A method for screening for a stimulating agent as defined herein, comprises contacting a tissue exhibiting neuro-, muscular-, and/or neuro-muscular-degenerative disease, with a candidate compound; and measuring activity in said tissue of an LKKTET (SEQ ID NO: 1) or LKKTNT (SEQ ID NO: 2) peptide, wherein an increase of activity of said peptide in said tissue, compared to a level of activity of said peptide in a corresponding tissue lacking said candidate compound, indicates that said compound is capable of inducing said stimulating agent.

comprising a peptide agent comprising amino acid sequence LKKTET (SEQ ID NO: 1) or a conservative variant thereof, Thymosin β4 (Tβ4), KLKKTET (SEQ ID NO: 3) or a conservative variant thereof, LKKTETQ (SEQ ID NO: 4) or a conservative variant thereof, so as to treat or reduce tissue deterioration, injury or damage caused by said at least one disease, or to restore tissue adversely affected by said at least one disease, wherein said disease is associated with an inflammatory disorder in said subject or wherein said disease comprises an inflammatory disorder in said subject, and wherein said disease is at least one of a disease of neurovascular cells or nervous tissue other than brain neurovascular cells or nervous tissue, multiple sclerosis (MS), spinal muscular atrophy (SMA), myasthenia gravis, transmissible spongiform encephalopathies (TSEs), bovine spongiform encephalopathy (BSE) or muscular dystrophy other than Duchenne muscular dystrophy.

The invention claimed is:

1. A method of treating or reducing deterioration of, injury to, or damage to a subject's tissue that is caused by at least one disease selected from a neuro-, muscular- or neuro-muscular-degenerative disease other than Duchenne muscular dystrophy, or restoring said subject's tissue that has been adversely affected by said at least one disease, comprising administering to said subject an effective amount of a composition 2. The method of claim 1 wherein said peptide agent is an anti-inflammatory agent.

3. The method of claim 1 wherein said peptide agent is thymosin beta 4 (Tβ4).

4. A method of treating or reducing deterioration of, injury to, or damage to a subject's tissue that is caused by at least one disease selected from a neuro-, muscular- or neuro-muscular-degenerative disease other than Duchenne muscular dystrophy, or restoring said subject's tissue that has been adversely affected by said at least one disease, comprising administering to said subject an effective amount of a composition comprising a peptide agent comprising amino acid sequence LKKTET (SEQ ID NO: 1) or a conservative variant thereof, Thymosin β4 (Tβ4), KLKKTET (SEQ ID NO: 3) or a conservative variant thereof, LKKTETQ (SEQ ID NO: 4) or a conservative variant thereof, so as to treat or reduce tissue deterioration, injury or damage caused by said at least one disease, or to restore tissue adversely affected by said at least one disease, wherein said peptide agent is other than Tβ4 and other than oxidized Tβ4, and wherein said disease is at least one of a disease of neurovascular cells or nervous tissue other than brain neurovascular cells or nervous tissue, multiple sclerosis (MS), spinal muscular atrophy (SMA), myasthenia gravis, transmissible spongiform encephalopathies (TSEs), bovine spongiform encephalopathy (BSE) or muscular dystrophy other than Duchenne muscular dystrophy.

5. The method of claim 1 wherein said peptide agent is administered to said subject at a dosage within a range of about 1-30 micrograms and at a concentration within the range of about 0.01-0.1% by weight.

6. The method of claim 1 wherein said agent is administered by direct administration to said tissue, or by intravenous, intraperitoneal, intramuscular, subcutaneous, inhalation, transdermal or oral administration, to said subject.

7. The method of claim 1 wherein said composition is administered systemically.

8. The method of claim 1 wherein said composition is administered directly.

9. The method of claim 1 wherein said composition is in the form of a solution, gel, creme, paste, lotion, spray, suspension, dispersion, salve, hydrogel or ointment formulation.

10. The method of claim 1 wherein said Tβ4 is a recombinant or synthetic peptide.

11. A method of treating or reducing deterioration of, injury to, or damage to a subject's tissue that is caused by at least one disease selected from a neuro-, muscular- or neuro-muscular-degenerative disease other than Duchenne muscular dystrophy, or restoring said subject's tissue that has been adversely affected by said at least one disease, comprising administering to said subject an effective amount of a composition comprising a peptide agent comprising amino acid sequence LKKTET (SEQ ID NO: 1) or a conservative variant thereof, Thymosin β4 (Tβ4), KLKKTET (SEQ ID NO: 3) or a conservative variant thereof, LKKTETQ (SEQ ID NO: 4) or a conservative variant thereof, so as to treat or reduce tissue deterioration, injury or damage caused by said at least one disease, or to restore tissue adversely affected by said at least one disease, wherein said disease is a muscular-degenerative disease.

12. A method of treating or reducing deterioration of, injury to, or damage to a subject's tissue that is caused by at least one disease selected from a neuro-, muscular- or neuro-muscular-degenerative disease other than Duchenne muscular dystrophy, or restoring said subject's tissue that has been adversely affected by said at least one disease, comprising administering to said subject an effective amount of a composition comprising a peptide agent comprising amino acid sequence LKKTET (SEQ ID NO: 1) or a conservative variant thereof, Thymosin β4 (Tβ4), KLKKTET (SEQ ID NO: 3) or a conservative variant thereof, LKKTETQ (SEQ ID NO: 4) or a conservative variant thereof, so as to treat or reduce tissue deterioration, injury or damage caused by said at least one disease, or to restore tissue adversely affected by said at least one disease, wherein said disease is a neuro-muscular-degenerative disease, and wherein said disease is at least one of a disease of neurovascular cells or nervous tissue other than brain neurovascular cells or nervous tissue, multiple sclerosis (MS), spinal muscular atrophy (SMA), myasthenia gravis, transmissible spongiform encephalopathies (TSEs), bovine spongiform encephalopathy (BSE) or muscular dystrophy other than Duchenne muscular dystrophy.

13. A method for screening for a stimulating agent that stimulates production of a peptide agent comprising amino acid sequence LKKTET (SEQ ID NO: 1) or a conservative variant thereof; LKKTNT (SEQ ID NO: 2) or a conservative variant thereof; Thymosin β4 (Tβ4); a Tβ4 isoform; KLKKTET (SEQ ID NO: 3); LKKTETQ (SEQ ID NO: 4); an N-terminal variant of Tβ4; a C-terminal variant of Tβ4; an agonist of Tβ4; oxidized Tβ4; Tβ4$^{ala}$; Tβ9; Tβ10; Tβ11; Tβ12; Tβ13; Tβ14; Tβ15; gelsolin; vitamin D binding protein (DBP); profiling; cofilin; depactin; DNaseI; vilin; fragmin; severin; capping protein; p-actinin; or acumentin, comprising contacting a tissue exhibiting neuro-, muscular-, and/or neuro-muscular-degenerative disease, with a candidate compound; and measuring activity in said tissue of an LKKTET (SEQ ID NO: 1) or LKKTNT SEQ ID NO: 2) peptide, wherein an increase of activity of said peptide in said tissue, compared to a level of activity of said peptide in a corresponding tissue lacking said candidate compound, indicates that said compound is capable of inducing said stimulating agent.

14. The method of claim 13 wherein said peptide is thymosin beta 4.

15. A method of treating or reducing deterioration of, injury to, or damage to a subject's tissue that is caused by at least one disease selected from a neuro-, muscular- or neuro-muscular-degenerative disease other than Duchenne muscular dystrophy, or restoring said subject's tissue that has been adversely affected by said at least one disease, comprising administering to said subject an effective amount of a composition comprising a peptide agent comprising amino acid sequence LKKTET (SEQ ID NO: 1) or a conservative variant thereof, Thymosin β4 (Tβ4), KLKKTET (SEQ ID NO: 3) or a conservative variant thereof, LKKTETQ (SEQ ID NO: 4) or a conservative variant thereof, so as to treat or reduce tissue deterioration, injury or damage caused by said at least one disease, or to restore tissue adversely affected by said at least one disease, wherein said disease is multiple sclerosis.

16. A method of treating or reducing deterioration of, injury to, or damage to a subject's tissue that is caused by at least one disease selected from a neuro-, muscular- or neuro-muscular-degenerative disease other than Duchenne muscular dystrophy, or restoring said subject's tissue that has been adversely affected by said at least one disease, comprising administering to said subject an effective amount of a composition comprising a peptide agent comprising amino acid sequence LKKTET (SEQ ID NO: 1) or a conservative variant thereof, Thymosin β4 (Tβ4), KLKKTET (SEQ ID NO: 3) or a conservative variant thereof, LKKTETQ (SEQ ID NO: 4) or a conservative variant thereof, so as to treat or reduce tissue deterioration, injury or damage caused by said at least one disease, or to restore tissue adversely affected by said at least one disease, wherein said method comprises treating damage to a subject's tissue caused by multiple sclerosis, and wherein said peptide agent comprises Tβ4.

17. A method of treating or reducing deterioration of, injury to, or damage to a subject's tissue that is caused by at least one disease selected from a neuro-, muscular- or neuro-muscular-degenerative disease other than Duchenne muscular dystrophy, or restoring said subject's tissue that has been adversely affected by said at least one disease, comprising administering to said subject an effective amount of a composition comprising a peptide agent comprising amino acid sequence LKKTET (SEQ ID NO: 1) or a conservative variant thereof, Thymosin β4 (Tβ4), KLKKTET (SEQ ID NO: 3) or a conservative variant thereof, LKKTETQ (SEQ ID NO: 4) or a conservative variant thereof, so as to treat or reduce tissue deterioration, injury or damage caused by said at least one disease, or to restore tissue adversely affected by said at least one disease, wherein said method comprises treating damage to a subject's tissue caused by a neuro-degenerative disease other than Duchenne muscular dystrophy, and wherein said peptide agent comprises Tβ4, and wherein said disease is at least one of multiple sclerosis (MS), spinal muscular atrophy (SMA), myasthenia gravis, transmissible spongiform encephalopathies (TSEs), or bovine spongiform encephalopathy (BSE).

18. The method of claim 11 wherein said peptide agent is thymosin beta 4 (Tβ4).

19. The method of claim 18 wherein said peptide agent is administered to said subject at a dosage within a range of about 1-30 micrograms and at a concentration within the range of about 0.01-0.1% by weight.

20. The method of claim 18 wherein said agent is administered by direct administration to said tissue, or by intravenous, intraperitoneal, intramuscular, subcutaneous, inhalation, transdermal or oral administration, to said subject.

21. The method of claim 18 wherein said composition is administered systemically.

22. The method of claim 18 wherein said composition is administered directly.

23. The method of claim 18 wherein said composition is in the form of a solution, gel, creme, paste, lotion, spray, suspension, dispersion, salve, hydrogel or ointment formulation.

24. The method of claim 18 wherein said Tβ4 is a recombinant or synthetic peptide.

25. The method of claim 18 wherein said disease is at least one of multiple sclerosis (MS), spinal muscular atrophy (SMA), myasthenia gravis, transmissible spongiform encephalopathies (TSEs), or bovine spongiform encephalopathy (BSE).

26. The method of claim 12 wherein said peptide agent is thymosin beta 4 (Tβ4).

27. The method of claim 26 wherein said peptide agent is administered to said subject at a dosage within a range of about 1-30 micrograms and at a concentration within the range of about 0.01-0.1% by weight.

28. The method of claim 26 wherein said agent is administered by direct administration to said tissue, or by intravenous, intraperitoneal, intramuscular, subcutaneous, inhalation, transdermal or oral administration, to said subject.

29. The method of claim 26 wherein said composition is administered systemically.

30. The method of claim 26 wherein said composition is administered directly.

31. The method of claim 26 wherein said composition is in the form of a solution, gel, creme, paste, lotion, spray, suspension, dispersion, salve, hydrogel or ointment formulation.

32. The method of claim 26 wherein said Tβ4 is a recombinant or synthetic peptide.

33. The method of claim 17 wherein said peptide agent is administered to said subject at a dosage within a range of about 1-30 micrograms and at a concentration within the range of about 0.01-0.1% by weight.

34. The method of claim 17 wherein said agent is administered by direct administration to said tissue, or by intravenous, intraperitoneal, intramuscular, subcutaneous, inhalation, transdermal or oral administration, to said subject.

35. The method of claim 17 wherein said composition is administered systemically.

36. The method of claim 17 wherein said composition is administered directly.

37. The method of claim 17 wherein said composition is in the form of a solution, gel, creme, paste, lotion, spray, suspension, dispersion, salve, hydrogel or ointment formulation.

38. The method of claim 17 wherein said Tβ4 is a recombinant or synthetic peptide.

* * * * *

UNITED STATES PATENT AND TRADEMARK OFFICE
CERTIFICATE OF CORRECTION

PATENT NO. : 8,716,215 B2
APPLICATION NO. : 11/813264
DATED : May 6, 2014
INVENTOR(S) : Goldstein et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1691 days.

Signed and Sealed this
Twenty-ninth Day of September, 2015

Michelle K. Lee
*Director of the United States Patent and Trademark Office*

```
                        SEQUENCE LISTING

<160> NUMBER OF SEQ ID NOS: 4

<210> SEQ ID NO 1
<211> LENGTH: 6
<212> TYPE: PRT
<213> ORGANISM: Homo sapiens

<400> SEQUENCE: 1

Leu Lys Lys Thr Glu Thr
1               5

<210> SEQ ID NO 2
<211> LENGTH: 6
<212> TYPE: PRT
<213> ORGANISM: Homo sapiens

<400> SEQUENCE: 2

Leu Lys Lys Thr Asn Thr
1               5

<210> SEQ ID NO 3
<211> LENGTH: 7
<212> TYPE: PRT
<213> ORGANISM: Homo sapiens

<400> SEQUENCE: 3

Lys Leu Lys Lys Thr Glu Thr
1               5

<210> SEQ ID NO 4
<211> LENGTH: 7
<212> TYPE: PRT
<213> ORGANISM: Homo sapiens

<400> SEQUENCE: 4

Leu Lys Lys Thr Glu Thr Gln
1               5
```